United States Patent [19]
Moseley

[11] Patent Number: 5,524,058
[45] Date of Patent: * Jun. 4, 1996

[54] APPARATUS FOR PERFORMING NOISE CANCELLATION IN TELEPHONIC DEVICES AND HEADWEAR

[75] Inventor: William T. Moseley, Shreveport, La.

[73] Assignee: MNC, Inc., Shreveport, La.

[ * ] Notice: The term of this patent sahll not extend beyond the expiration date of Pat. No. 5,138,663.

[21] Appl. No.: 180,346

[22] Filed: Jan. 12, 1994

[51] Int. Cl.$^6$ .................................................. G10K 11/16
[52] U.S. Cl. .................................................. 381/71; 381/72
[58] Field of Search .............................. 381/71–72, 163, 381/150; 181/151, 166, 198

[56] References Cited

U.S. PATENT DOCUMENTS

| | | | |
|---|---|---|---|
| 1,655,267 | 1/1928 | Hahnemann et al. | 181/166 |
| 2,972,018 | 2/1961 | Hawley et al. | 381/72 |
| 3,009,991 | 11/1961 | Beckey | 381/72 |
| 3,278,695 | 10/1966 | Craig et al. | 381/163 |
| 3,562,429 | 2/1971 | West | 381/72 |
| 3,890,474 | 6/1975 | Glicksberg | 381/72 |
| 3,922,488 | 11/1975 | Gabr | 381/72 |
| 3,952,158 | 4/1976 | Kyle et al. | 381/72 |
| 4,025,724 | 5/1977 | Davidson, Jr. et al. | 381/72 |
| 4,195,360 | 3/1980 | Fothergill | 381/72 |
| 4,284,844 | 8/1981 | Belles | 381/90 |
| 4,439,644 | 3/1984 | Bruney, III | 381/158 |
| 4,455,675 | 6/1984 | Bose | 381/72 |
| 4,504,703 | 3/1985 | Schmeiter et al. | 381/163 |
| 4,644,581 | 2/1987 | Sapiejewski | 381/72 |
| 4,654,871 | 3/1987 | Chaplin et al. | 381/72 |
| 4,677,677 | 6/1986 | Eriksson | 381/72 |
| 4,833,719 | 5/1989 | Carme et al. | 381/72 |
| 4,928,311 | 5/1990 | Trompler | 381/72 |
| 4,953,217 | 8/1990 | Twiney et al. | 381/72 |
| 4,972,491 | 11/1990 | Wilcox, Jr. | 381/72 |
| 5,001,763 | 3/1991 | Moseley | 381/71 |
| 5,117,461 | 5/1992 | Moseley | 381/71 |
| 5,134,659 | 6/1992 | Moseley | 381/71 |
| 5,138,663 | 8/1992 | Moseley | 381/71 |

FOREIGN PATENT DOCUMENTS

| | | |
|---|---|---|
| 212840 | 3/1987 | European Pat. Off. . |
| 2925134 | 1/1981 | Germany . |
| 1530814 | 1/1978 | United Kingdom . |
| 2172769 | 9/1986 | United Kingdom . |
| 8912432 | 12/1989 | WIPO . |

OTHER PUBLICATIONS

John Free, "Noise Zapper", Popular Science, Jan. 1987, pp. 76, 77, 96.

Primary Examiner—Stephen Brinich
Attorney, Agent, or Firm—Cushman Darby & Cushman

[57] ABSTRACT

A noise cancellation module is combined with a telephone handset or article of headwear to cancel a selected frequency or range of frequencies so as to enable a user to better use the handset and function with the headwear in place.

10 Claims, 1 Drawing Sheet

APPARATUS FOR PERFORMING NOISE CANCELLATION IN TELEPHONIC DEVICES AND HEADWEAR

FIELD OF THE INVENTION

The present invention relates to electroacoustic devices for performing noise cancellation in conjunction with the use of telephonic hand sets and headwear.

DESCRIPTION OF RELATED ART

In prior commonly assigned U.S. Pat. Nos. 5,001,763, 5,117,461, 5,134,659 and 5,138,663, there are disclosed arrangements for effecting cancellation of undesired sound in conjunction with an ear piece such as an audio head phone that are in widespread use in the music and audio fields. In these prior structures, the ear canal was substantially surrounded but not necessarily isolated by the use of a shielding cover or soft cushion and this was believed to facilitate noise cancellation of the desired or selected frequency or range of frequencies that the user needed to either attenuate or eliminate and which resulted from environmental factors such as noise generated in connection with operating machinery or during flight in a plane. In one embodiment, a first transducer was employed in the ear covering and directed outwardly to detect the environmental noise it was desired to cancel. A second transducer in one embodiment was directed inwardly toward the ear canal. A third transducer in one embodiment had two input transducers facing in opposite directions, one toward the noise source and the other toward the ear canal. The disclosed circuitry operated a speaker which emitted a cancelling sound wave into the ear canal that was substantially 180° out of phase from a selected frequency of the sound detected by the outwardly and inwardly directed sensing transducers which were usually electret microphones. The configuration and position relationship of the transducers provided a significant degree of efficiency when compared to other devices available in the prior art.

In general, many such devices including those in my earlier patents provide a composite transducer assembly with an input transducer and the output transducer as noted above. Due to the fact that transducers are not ideal, particularly the small electret microphones as well as the small headphone type speakers in which one or both may not operate at ideal design parameters, it is necessary to compensate in the enabling circuitry to provide an efficient noise cancelling operation. These concerns are well addressed in U.S. Pat. Nos. 5,001,763, 51174561 and 5,134,659 and the disclosures of these patents are incorporated herein by reference.

While the prior efforts have been directed to the use of the above-mentioned type transducers mounted in a structure that substantially encloses both ears in use, such as a headset, it has been found that a distinct need exists for noise cancellation in conjunction with the use of an ordinary telephone handset or other headwear where only one ear is exposed to a speaker and the other ear is left open to the surrounding environmental noise. In this regard, many will be familiar with the difficulty of hearing using a public phone in a large hall or enclosure such as an airport or train terminal where a broad range of frequencies are generated and which greatly complicate clear communication over a telephone handset as well as a mobile telephone unit. In many activities where helmets or other types are headwear are customarily worn, hearing is diminished by the helmet or headwear as well as by noise generated in the surrounding environment such as a sports stadium, in civil or military disturbances or the like.

SUMMARY OF THE INVENTION

The present invention endeavors to solve the foregoing difficulty by providing a noise cancellation device installed in a telephone handset and in certain types of headwear and, specifically, in the ear piece portion of the handset to enable a user to more clearly communicate using either a conventional hardwired telephone handset as well as a cellular unit in conditions that are less than favorable for clear communication using such implements. To this end, the handset will incorporate transducers oriented as specified in either U.S. Pat. No. 5,001,763 or U.S. Pat. No. 5,117,461 or U.S. Pat. No. 5,134,659 with the circuitry modified to enable connection with the normal communication circuit whereby the user will be able to enjoy relatively clear communications by virtue of the suppression of sound wave interference from external sources as discussed in the above-identified U.S. patents. In addition, the present invention contemplates the incorporation of a noise suppression circuit including the aforementioned transducers in a helmet for use by a cyclist or an athletic helmet to enable clear communication of required information.

BRIEF DESCRIPTION OF THE DRAWINGS

The foregoing and other advantages will become apparent as consideration is given to the following detailed description taken in conjunction with the accompanying drawings, in which.

DETAILED DESCRIPTION OF THE INVENTION

Figure 1:
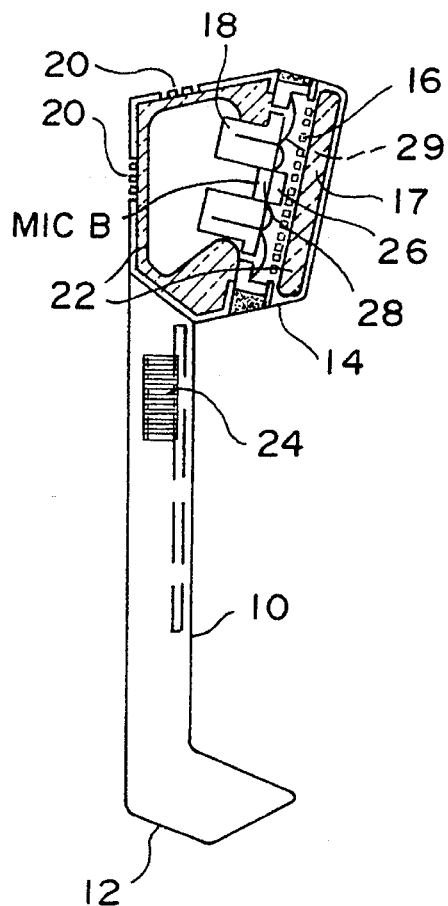
FIG. 1 is a side view and elevation, partly in section of one embodiment of a telephone hand set incorporating the present invention.

Referring to the drawings wherein like numerals designate corresponding parts throughout the several views, there is shown in FIG. 1 a typical telephone handset 10 which includes the conventional mouth piece section 12 and an ear piece section 14.

In the ear piece section 14, a transducer mounting baffle is provided immediately below a suitable sound absorbent material 22, such as foam, and the outer ear piece section 14. The rear interior cavity of the ear piece section 14 is also lined with a suitable sound absorbent material 22 and is provided with air vents such as 20 to acoustically balance the performance of the transducer in a particular telephone handset 10 and to allow external noise to reach the microphone 28. Within the ear piece section 14, two microphones are mounted facing in opposite directions as at 26 and 28 with the operative surfaces of the microphones 26 and 28 lying in substantially the same plane. In addition, transducer 18 which may be annular and surround the microphones 26 and 28 as shown, is provided to supply sound to the users ear. If desired, a volume control such as at 24 may be provided and may be of the conventional type.

Figure 2:
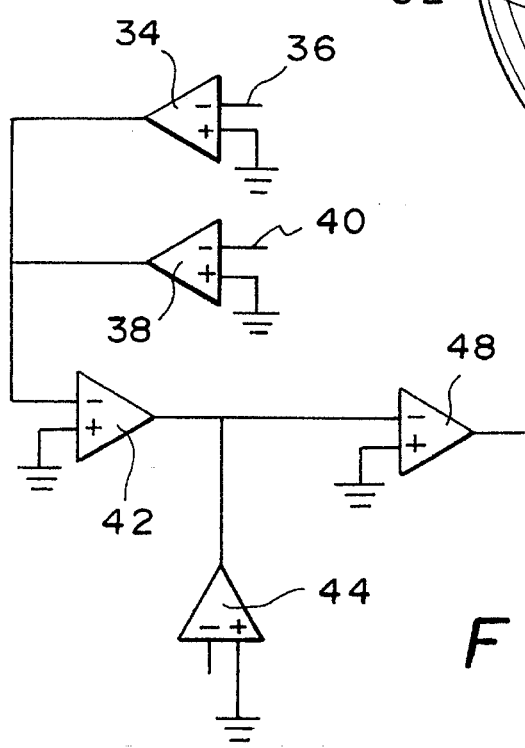
FIG. 2 is an illustration of one embodiment of a circuit incorporating the hand set signal input to enable normal communication through the hand set even when furnished with the noise suppression or cancellation circuitry of the present invention.

In FIG. 2 there is shown a simplified circuitry for the hand set construction of FIG. 1. Specifically, a preamp circuit 34 receives its input through line 36 from microphone 26 while preamplifier circuit 38 receives its input through line 40 from transducer microphone 28 which faces the interior of the hand set 14. These signals are combined in a mixing amplifier 42. The hand set signal input from the telephone line or other communications source is received through preamplifier 44 from which it is fed to amplifier 48 to transducer 18.

As fully explained in my prior U.S. Pat. Nos. 5,001,763, 5,117,461 and 5,134,659, the amplifiers are set so that the sound received by transducer microphones 26 and 28 are mixed so that they maximize cancellation in the ear piece 14 when pressed by the user against the ear.

With this arrangement just as provided in my prior U.S. Pat. Nos. 5,117,461 and 5,134,659, microphone 26 which will face the ear canal when the ear piece 14 is pressed by the user against his ear will detect any residual uncancelled noise present inside the ear canal cavity while the outwardly facing transducer microphone 28 will detect, to a large extent, the external surrounding noise. The transducer 18 can therefore be most effectively activated to provide a cancelling, that is, phase shifted, sound wave to the ear canal while the ear piece 14 is being used against the ear of the individual.

Figure 3:
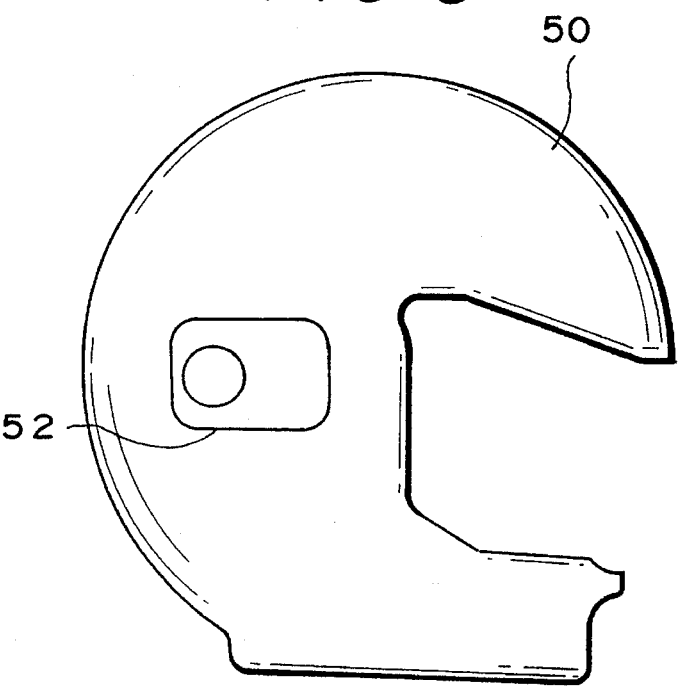
FIG. 3 is a side view of helmet with a noise suppression module inserted to be adjacent one or both ears of the user.

As shown in FIG. 3, a type of headwear in the form of a helmet 50 is illustrated where an ear piece 52 has been inserted and is carried on the helmet adjacent the ear of a user when the helmet is worn by the user. One for each ear may be provided but in some applications, a single ear piece circuit may, of course, be provided. Each unit 52 includes the dual oppositely facing microphones 26 and 28 as in FIG. 1 together with the accompanying circuitry to effect phase shifting of sounds received by the microphones 26 and 28 to deaden selected sound frequencies. Such an arrangement in a helmet such as that illustrated in FIG. 3 would be particularly useful during high speed racing where engine noise could interfere with the hearing perception of the driver. Similarly, in emergency situations where public officials such as police and firemen use helmets as well as in an athletic event such as football or similar contest, it is necessary for police, firemen, coaches or managers to communicate with personnel or players in a crowded stadium. In such circumstances, the use of a helmet with a sound cancellation ear piece 52 for at least one of the ears of the user would be extremely useful in deadening crowd noise for which the circuitry such as that shown in FIG. 2 could be previously adjusted to accommodate.

While the helmet 50 illustrated in FIG. 3 is one example of an application of the noise suppression technology of the present invention, it will be appreciated by those skilled in the art that other types of helmets and head wear may also be employed and are within the scope of the present invention.

Having described the invention, it will also be apparent to those skilled in this art that various modifications may be made thereto without departing from the spirit and scope of this invention as defined in the appended claims.

What is claimed is:

1. A telephonic unit having an audio input portion and an audio output portion, said audio output portion including a composite transducer assembly for cancelling noise in an ear canal when the composite transducer assembly is in use with said audio output portion adjacent a user's ear, comprising a composite transducer for generating an opposing sound wave which propagates from the composite transducer in a direction into the ear canal, the opposing sound wave being generated to have an amplitude substantially equal to the amplitude of the noise in the ear canal, the opposing sound wave being generated to be substantially 180° out of phase with respect to at least some of the frequencies of the noise in said ear canal and including two microphones having operative surfaces lying in substantially the same plane and facing in opposite directions from one another.

2. The invention as claimed in claim 1 wherein said audio output portion is connected to a telephone line.

3. The invention as claimed in claim 2 wherein said audio input portion is connected to the telephone line.

4. The invention as claimed in claim 1 wherein said audio output portion is connected to a radio wave receiver.

5. The invention as claimed in claim 4 wherein said audio input portion is connected to a radio wave transmitter.

6. The invention as claimed in claim 1 wherein said audio input portion is connected to the signal line of a paging system utilizing a telephone type handset.

7. A head wear article having an ear piece including a composite transducer assembly for cancelling noise in an ear canal when the composite transducer assembly is in use, comprising:

a composite transducer for generating an opposing sound wave which propagates from the composite transducer in a direction into the ear canal, the opposing sound wave being generated to have an amplitude substantially equal to the amplitude of the noise in the ear canal, the opposing sound wave being generated to be substantially 180° out of phase with respect to at least some of the frequencies of the noise in said ear canal, and including two microphones having operative surfaces lying in substantially the same plane but facing in opposite directions from one another.

8. The invention as claimed in claim 7 wherein said article is a helmet.

9. The invention as claimed in claim 7 wherein said article includes a covering for each ear and each covering carries a composite transducer assembly.

10. A telephonic unit having an audio input portion and an audio output portion, said audio output portion including a composite transducer assembly for cancelling noise in an ear canal when the composite transducer assembly is in use with said audio output portion adjacent a user's ear, said unit comprising a composite transducer for generating an opposing sound wave which propagates from the composite transducer in a direction into the ear canal, the opposing sound wave being generated to have an amplitude substantially equal to the amplitude of the noise in the ear canal, the opposing sound wave being generated to be substantially 180° out of phase with respect to at least some of the frequencies of the noise in said ear canal and including two microphones having operative surfaces lying in substantially the same plane.

* * * * *